United States Patent [19]

New et al.

[11] Patent Number: 5,137,894
[45] Date of Patent: Aug. 11, 1992

[54] 4-(4-PIPERIDINYL-THIENO[3,2-C]PYRIDINE DERIVATIVES OF N-ALKYLGLUTARIMIDES

[76] Inventors: James S. New, 45 Wellington Ct., Belle Mead, N.J. 08502; William L. Christopher, 103 Charlesberry La., Chapel, N.C. 27514

[21] Appl. No.: 804,270

[22] Filed: Dec. 5, 1991

[51] Int. Cl.⁵ ............... C07D 471/04; C07D 471/10; A61K 31/44
[52] U.S. Cl. ..................... 514/301; 514/278; 546/16; 546/114
[58] Field of Search .............. 546/114, 16; 514/278, 514/301

[56] References Cited

U.S. PATENT DOCUMENTS

| | | | |
|---|---|---|---|
| 3,398,151 | 8/1968 | Wu et al. | 514/230 |
| 3,717,634 | 2/1973 | Wu et al. | 514/230 |
| 3,907,801 | 9/1975 | Wu et al. | 514/230 |
| 4,320,131 | 3/1982 | Temple et al. | 514/278 |
| 4,677,104 | 6/1987 | New et al. | 514/222 |

*Primary Examiner*—Alan L. Rotman
*Assistant Examiner*—Barbara Twardzik
*Attorney, Agent, or Firm*—Richard P. Ryan

[57] ABSTRACT

Novel thieno[3,2-c]pyridine derivatives of Formula I,

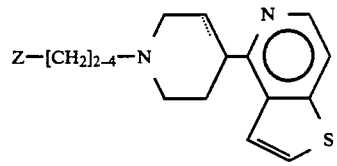

in which Z is glutarimide, are useful antipsychotic agents with reduced side-effect liability.

12 Claims, No Drawings

4-(4-PIPERIDINYL-THIENO[3,2-C]PYRIDINE DERIVATIVES OF N-ALKYLGLUTARIMIDES

FIELD OF THE INVENTION

The invention is concerned with drug bioaffecting body-treating compounds comprised of piperidines and 1,2,5,6-tetrahydropyridines substituted at the 4-carbon position with a 4-thieno[3,2-c]pyridine ring and at the nitrogen with a glutarimidinylalkyl moiety. These compounds and their pharmaceutically acceptable salts and/or hydrates possess useful antipsychotic activity.

BACKGROUND OF THE INVENTION

The compounds of the present invention appear most closely related to a series of antipsychotic piperazine compounds of structure 1 disclosed by New, et al., in U.S. Pat. No. 4,677,104;

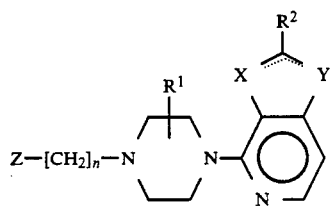

1 wherein, inter alia, Z is a glutarimide moiety and the fused ring pyridine system is thienopyridine. Z is connected to a piperazine nitrogen atom by a $C_2$ to $C_4$ alkylene chain. In the present invention the piperazine ring has been replaced by either a piperidine or a 1,2,5,6-tetrahydropyridine ring system.

Temple, et al., disclosed 4-phenyltetrahydropyridinyl and 4-phenyl-4-hydroxypiperazinyl derivatives of N-alkylazaspiro-decanediones and - undecanediones of structure 2 in U.S. Pat. No. 4,320,131.

2

These compounds were described as tranquilizers having some anxioselective and neuroleptic actions.

SUMMARY OF THE INVENTION

The invention concerns novel piperidine and tetrahydropyridine compounds of Formula I

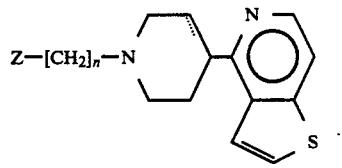

I wherein Z is a glutarimide moiety, n is an integer from 2 to 4, and the full and dotted lines signify the location of either a carbon-carbon single bond or double bond. Pharmaceutically acceptable salts and/or solvates of Formula I compounds are also encompassed in the invention and all are intended for use as antipsychotic medicaments in patients in need of such treatment.

DETAILED DESCRIPTION OF THE INVENTION

In its broadest aspect, the present invention is concerned with piperidinyl and 1,2,5,6-tetrahydro-pyridinyl derivatives having antipsychotic properties. These derivatives are characterized by Formula I and include pharmaceutically acceptable acid addition salts and/or solvates.

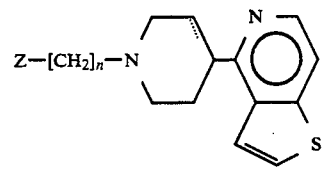

I

In the structure of the compound of Formula I, Z

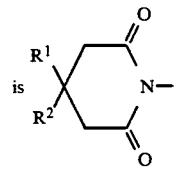

is wherein $R^1$ and $R^2$ are independently selected from hydrogen and $C_{1-4}$ alkyl or $R^1$ and $R^2$, taken together, represent a $C_4$ or $C_5$ alkylene bridge thereby forming a 5,6 or 6,6- spiro ring system. The symbol n denotes an integer from 2 to 4, thereby describing an ethyl, propyl or butyl alkylene linkage between the glutarimide and piperidine nitrogen atoms. The dotted line accompanying the full line indicates either a single or double carbon-carbon bond, giving consequently either a piperidine ring or a 1,2,5,6-tetrahydropyridine system. Preferred compounds are those in which $R^1$ and $R^2$ are independently selected from hydrogen and $C_{1-4}$ lower alkyl and n is 4. Most preferred compounds are those in which both $R^1$ and $R^2$ are $C_{1-4}$ lower alkyl.

The pharmaceutically acceptable acid addition salts of the invention are those in which the anion does not contribute significantly to the toxicity or pharmacological activity of the salt and, as such, they are the pharmacological equivalents of the bases of the Formula I compounds. They are generally preferred for medical usage. In some instances, they have physical properties which make them more desirable for pharmaceutical formulation. Such properties can be solubility, lack of hygroscopicity, compressibility with respect to tablet formation and compatibility with other ingredients with which the substance may be used for pharmaceutical purposes. The salts are routinely made by admixture of a Formula I base with a selected acid, preferably by contacting solutions employing an excess of commonly used inert solvents such as ether, benzene, ethanol, ethyl acetate, acetonitrile and water. The salt form may also be prepared by any of the other standard methods detailed in the literature and available to any practitioner skilled in the art. Some examples of useful organic acids are the carboxylic acids such as maleic acid, acetic acid, tartaric acid, propionic acid, fumaric acid, isethionic acid, succinic acid, pamoic acid, cyclamic acid, pivalic acid, and the like; useful inorganic acids may be hydrohalide acids such as HCl, HBr, HI; sulfuric acids; phosphoric acids; and the like.

The compounds of the instant invention are useful pharmacological agents with psychotropic properties. In this regard, they exhibit selective central nervous system activity at non-toxic doses and are of particular interest as antipsychotic (neuroleptic) agents. As with other known antipsychotics, the compounds of Formula I evoke certain responses when studied in standard in vivo and in vitro pharmacological test systems which are known to correlate well with the relief of symptoms of acute and chronic psychosis in man.

For subclassification of the psychotropic activity and specificity of the instant compounds, state of the art in vitro central nervous system receptor binding methodology is employed. Certain compounds (commonly referred to as ligands) have been identified which preferentially bind to specific high affinity sites in brain tissue dealing with psychotropic activities or potential for side effects. Inhibition of radiolabeled ligand binding to such specific high affinity sites is considered a measure of a compound's ability to effect corresponding central nervous system function or to cause side effects in vivo. This principle is employed in tests, such as, for example, measuring inhibition of [$^3$H]spiperone binding which indicates significant dopamine receptor binding activity (cf: Burt, et al., Molecular Pharmacology, 12, 800 (1976); Science, 196, 326 (1977); Crease, et al., Science, 192, 481 (1976)).

Some of the more important binding tests employed are listed below in Table 1.

TABLE 1

| Receptor Binding Tests | | | |
|---|---|---|---|
| Test No. | Putative Receptor Site | Ligand Used | Specific Binding Agent |
| 252A | Dopamine/spiperone/ neuroleptic | [$^3$H] Spiperone | D(+)-Butaclamol |
| 252B | Alpha-1 | [$^3$H] WB-4101 | Phentolamine |
| 252E | Serotonin Type 1 (5-HT$_1$) | [$^3$H] 5-HT | 5-HT |
| 252I | Serotonin Type 2 (5-HT$_2$) | [$^3$H] Spiperone | D-Lysergide |

References:
252A - given supra
252B - Crews, et al., Science, 202:322, 1978 Rosenblatt et al., Brain Res., 160-186, 1979, U'Prichard, et al., Science, 199:197, 1978: Molec. Pharmacol., 13:454, 1977.
252E - Bennett and Snyder, Molec. Pharmacol., 12:373, 1976.
252I - Peroutka and Snyder, Molec. Pharmacol. 16:687, 1979.

Data derived from the above binding tests demonstrate that the family of compounds of the instant invention has modest to low affinity for dopaminergic receptors but much greater affinities for both serotonin $S_1$ and $S_2$ sites. These binding properties distinguish the instant compounds from the cited prior art compounds as well as most of the clinically useful antipsychotic agents now being used. In this regard, the instant compounds have some pharmacological properties in common with the atypical standard neuroleptic agent, clozapine, a dibenzodiazepine compound. The lack of dopaminergic binding affinities of the subject compounds is felt to relate to reduced liability to induce the unwanted extrapyramidal side effects common to most currently used antipsychotic agents.

Binding activity at the alpha-1 receptor (Test 252B) indicates that the compounds of the present invention will probably possess a sedating component of activity which is often desirable in the treatment of subgroups of psychotic patients.

The following in vivo test systems are conventionally used to classify and differentiate a psychotropic agent from a non-specific CNS depressant and to determine potential side-effect liabilities such as cataleptic activity.

TABLE 2

1. In Vivo Tests Used to Evaluate Formula I Compounds

Conditioned Avoidance Response (CAR)—measure of a drug's tranquilizing activity as determined by its attenuation of avoidance response to electrical shock in trained fasted rats cf: Albert, Pharmacologist, 4, 152 (1962); Wu, et al., J. Med. Chem., 12,876–881 (1969).

2. Catalepsy—drug-induced catalepsy in rats is predictive of potential extrapyramidal symptoms (EPS) in man. of: Costall, et al., Psychopharmacologia, 34, 233–241 (1974); Berkson, J. Amer. Statist. Assoc., 48, 565–599 (1953).

According to the pharmacological profile established by these in vivo tests, the instant compounds of Formula I have promising antipsychotic potential in that they are relatively potent in the CAR test, having oral ED$_{50}$ values <100 mg/kg body weight. The instant family of compounds may be considered to have selective antipsychotic activity inasmuch as antipsychotic activity is seen at doses which do not produce catalepsy. The significance of the effects of these compounds of the instant invention on catalepsy induction are better appreciated when one considers that antipsychotic agents as a class are known to produce extrapyramidal reactions. These unwanted extra-pyramidal reactions represent a serious treatment liability and comprise acute torsion dystonia, akathesia, Parkinsonism, and tardive dyskinesia.

In summary of the foregoing discussion, the instant compounds have psychotropic properties particularly suited to their use as selective antipsychotic agents with little potential for movement disorder side effects. Thus, another aspect of the instant invention concerns a process for ameliorating a psychotic state in a mammal in need of such treatment which comprises systemic administration to such mammal of an effective dose of a Formula I compound or a pharmaceutically acceptable acid addition salt and/or solvate thereof.

The administration and dosage regimen of compounds of Formula I is considered to be done in the same manner as for the reference compound clozapine, cf: The Merck Index, 11th Edition, (1989), page 379, and references therein. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 50 mg/kg, preferably, 0.1 to 2 mg/kg, when administered parenterally; and from about 1 to about 50 mg/kg, preferably 2 to 30 mg/kg, when administered orally. In some instances, a sufficient therapeutic effect can be obtained at lower doses while in others, larger doses will be required. The term "systemic administration" as used herein refers to oral, rectal, and parenteral, i.e., intramuscular, intravenous, and subcutaneous routes.

Generally, it will be found that when a compound of the present invention is administered orally, which is the preferred route, a larger quantity of the active agent is required to produce the same effect as a smaller quantity when given parenterally. In accordance with good clinical practice, it is preferred to administer the instant compounds at a concentration level that will produce effective antipsychotic effects without causing any harmful or untoward side effects.

Therapeutically, the instant compounds are generally given as pharmaceutical compositions comprised of an effective antipsychotic amount of a compound of Formula I or a pharmaceutically acceptable acid addition salt and/or solvate thereof and a pharmaceutically acceptable carrier. Pharmaceutical compositions for effecting such treatment will contain a major or minor amount, e.g. from 95 to 0.5% of at least one compound of the present invention in combination with a pharmaceutical carrier, the carrier comprising one or more solids, semi-solid, or liquid diluent, filler, and formulation adjuvant which is non-toxic, inert and pharmaceutically acceptable. Such pharmaceutical compositions are preferably in dosage unit forms; i.e., physically discrete units containing a pre-determined amount of the drug corresponding to a fraction or multiple of the dose which is calculated to produce the desired therapeutic response. The dosage units can contain one, two, three, four or more single doses; or alternatively, one-half, one-third, or one-fourth of a single dose. A single dose preferably contains an amount sufficient to produce the desired therapeutic effect upon administration at one application of one or more dosage units according to the pre-determined dosage regimen, usually a whole, half, third, or quarter of a daily dosage administered once, twice, three or four times a day. Other therapeutic agents can also be present. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch), and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propylene glycol, and polyethylene glycols or mixtures thereof. The polyethylene glycols consist of a mixture of non-volatile, usually liquid, polyethylene glycols which are soluble in both water and organic liquids and which have molecular weights of from about 200 to 1500.

The compounds of Formula I are obtained by procedures involving alkylation of piperidinyl or 1,2,5,6-tetrahydropyridinyl intermediates with glutarimidinylalkyl derivatives.

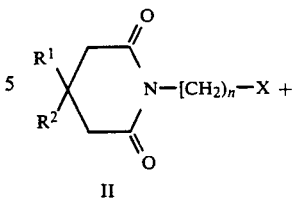

II

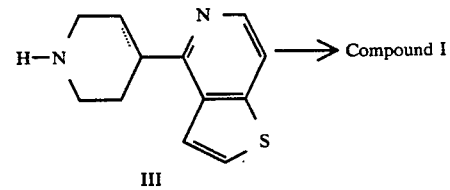

III

Process 1

In Process 1; $R^1$, $R^2$ and n have the same meanings as previously assigned supra. The symbol "X" in Process 1 is a suitable displacement group such as chloride, bromide, iodide, sulfate, phosphate, tosylate or mesylate. Process 1 is carried out under reaction conditions suitable for the preparation of tertiary amines by alkylation of secondary amines. The reactants are heated in a suitable organic liquid, preferably at temperatures of about 60 to about 100° C., in the presence of an acid binding agent. Benzene, dimethyl formamide, ethanol, acetonitrile, toluene and n-butyl alcohol are preferred examples of the liquid organic reaction media. The preferred acid binding agent is potassium carbonate, but other inorganic and tertiary organic bases may be employed including other alkali and alkaline earth metal carbonates, bicarbonates, or hydrides, and the tertiary amines. All of these synthetic methods have been fully described in the chemical literature and would be known to one skilled in the art of synthetic organic chemistry.

The intermediate compounds of Formula III may be conveniently prepared as shown in Processes 2 and 3. These processes may be modified according to the specific compounds desired.

Process 2

Preparation of Formula III Piperidines

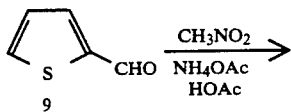

9

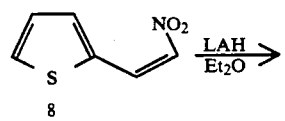

8

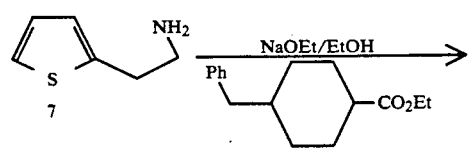

7

-continued
Process 2

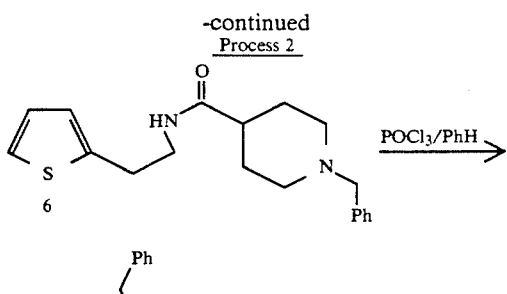

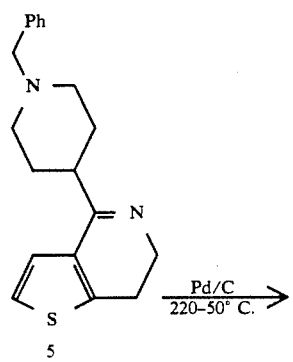

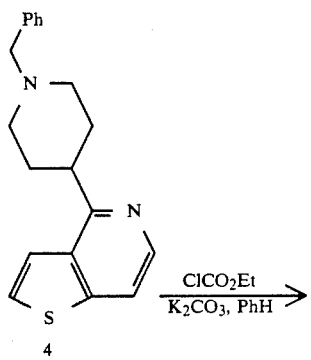

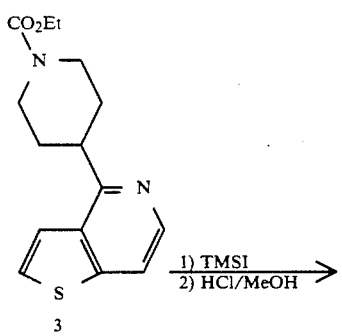

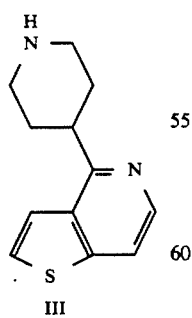

III

In Process 2, commercially available 2-thiophenecarboxaldehyde and nitromethane are condensed to produce compound 8 which is reduced to 7 via lithium aluminum hydride. Reaction of compound 7 with ethyl 1-benzyl-4-piperidinecarboxylate in ethoxide/ethanol generates the amide intermediate 6. The piperidine carboxylate reagent is prepared by benzylation of commercially available ethyl isonipecotate. Gentle refluxing of compound 6 in POCl₃/ benzene causes cyclization to compound 5. Catalytic dehydrogenation is effected neat with 5% palladium on carbon at 220°–250° to produce 4. Due to difficulty of debenzylation of 4, a conversion to the ethyl carbonate 3 was done with ethyl chloroformate in refluxing benzene, followed by sequential conversion to the trimethylsilyl ester with trimethylsilyl iodide and subsequent acidic work-up to yield the desired piperidine intermediate III.

Process 3

Preparation of Formula III Tetrahydropyridines

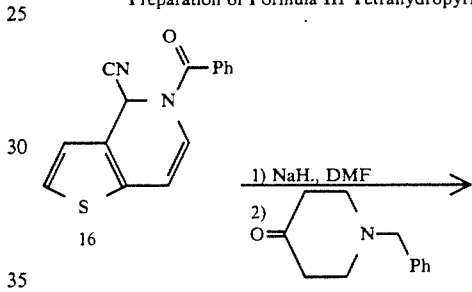

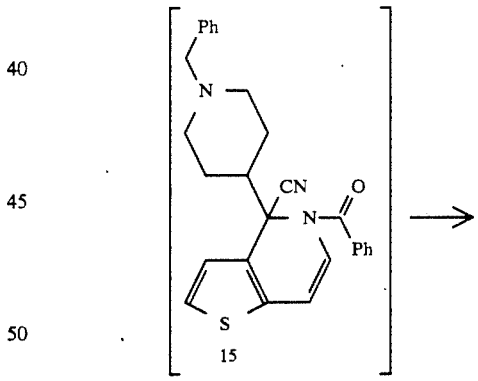

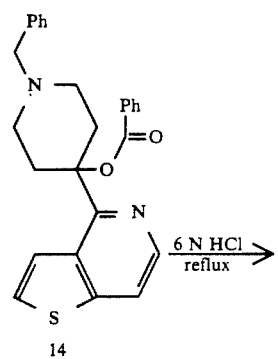

-continued
Process 3

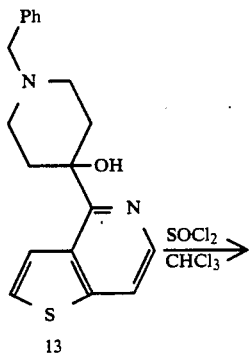

13

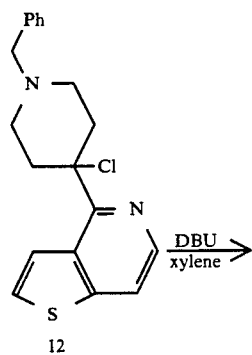

12

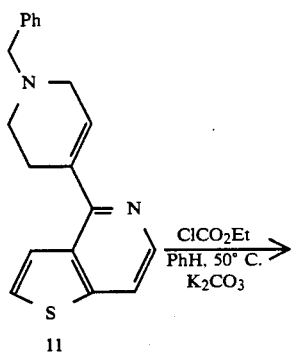

11

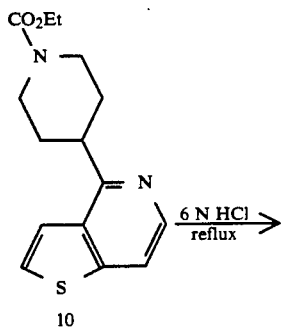

10

-continued
Process 3

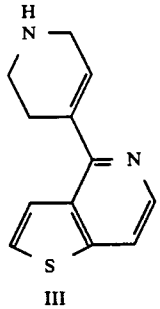

III

In Process 3 the Reissert compound 16 is treated sequentially with sodium hydride followed by 1-benzyl-4-piperidone which proceeds through intermediate 15 to the benzoate compound 14. Refluxing in 6N HCl results in quantitative conversion to the hydroxy compound 13 which was surprisingly inert to dehydration. As a result, 13 was converted to the chloro intermediate 12 which was successfully dehydrohalogenated to compound 11 by treatment with 1,8-diazabicyclo [5.4.0]undec-7-ene (DBU). Conversion of 11 to the carbamate 10 followed by acidic hydrolysis provided the desired 1,2,5,6-tetrahydro-pyridine intermediate III.

Syntheses of intermediate compounds of Formula II have been adequately disclosed in the chemical and patent literature, e.g., Wu, et al., U.S. Pat. No. 3,717,634; Temple, et al., U.S. Pat. No. 4,361,565. One convenient synthesis involves reaction of an appropriate glutaric anhydride with 4-aminobutanol in a heated reaction-inert organic solvent. The hydroxy function of the intermediary glutarimidinylalkanol is subsequently converted to the leaving groups X according to conventional techniques, thereby providing Formula II intermediates.

Utilization of the intermediate compounds of Formula II and III in Process 1 described above results in synthesis of the antipsychotic compounds of Formula I.

DESCRIPTION OF SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C. when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton (PMR) spectral data corresponds to the number of hydrogen atoms of a particular functional type in the molecule. The nature of the shift as to multiplicity is reported as broad singlet (bs), singlet (s), multiplet (m), doublet (d), doublet of doublets (dd), triplet (t), or quartet (q). Abbreviations employed are DMSO-$d_6$ (dimethyl-$d_6$-sulfoxide), CDCl$_3$ (chloroform-d) and are otherwise conventional. The infrared (IR) spectral descriptions include only absorption wave numbers (cm$^{-1}$) having functional group identification value. The IR determinations were employed using potassium bromide (KBr) as diluent. All compounds gave satisfactory ($\pm$ 0.40%) elemental analysis.

Synthesis of Intermediate of Formula III

EXAMPLE 1

Piperidine Intermediates

A.—Preparation of Thiophene Ethylamine 7

A solution of 2-thiophene carboxaldehyde, (9, 100 g, 1.0 equiv), nitromethane (2.0 equiv) and ammonium acetate (1.3 equiv) in 1 L acetic acid were refluxed until TLC examination indicated consumption of aldehyde (ca. 3 h). The reaction was cooled to 5° C. and carefully poured into 1 L ice-water. The green solid that precipitated was collected by filtration and dried in a desiccator overnight. The compound was dissolved in methylene chloride, dried over magnesium sulfate, filtered and evaporated in vacuo to a solid. This solid was dissolved in chloroform and filtered through a thick pad of silica gel to remove contaminant materials. The resultant solution was concentrated in vacuo to afford 2-thienyl nitrostyrene 8 as a green-yellow solid (82 g, 60%).

The nitro compound 8 was dissolved in diethyl ether and slowly added through a dropping funnel to a 0° C. stirring suspension of lithium aluminum hydride (60 g, 3 equiv) in ether. The addition was carefully monitored so as to maintain a slow reflux of the reaction mixture. Upon completion of addition, the reaction was allowed to stir for an additional 2 h in an ice-water bath. The excess LAH was quenched by slow addition of 60 mL water, 60 mL 3N NaOH and then by 180 mL water. The resulting mixture was filtered and collected salts were washed thoroughly with ether. The liquors were concentrated in vacuo to a dark oil which was distilled bulb-to-bulb to afford 7 as a clear oil (45.0 g, 67%).

B.—Preparation of Amide 6

Sodium ethoxide (2 equiv) was prepared in 500 mL ethanol from sodium metal (23 g). Thiophene ethylamine (7, 1 equiv) and the appropriate piperidinecarboxylate (1 equiv) were added and the resultant solution was refluxed until TLC examination indicated the reaction was complete (typically 12 h). A small amount of water was added to neutralize excess ethoxide and the reaction was concentrated in vacuo.

Utilizing ethyl 1-benzyl-4-piperidinecarboxylate, the above procedure afforded crude amide 6 as an off-white gum. The product was purified by recrystallization from diethyl ether to a white solid (47% yield). $^1$H NMR (200 MHz, CDCl$_3$) δ 7.32 (m, 5H), 7.14 (d, 1H), 6.91 (m, 1H), 6.80 (m, 1H), 5.85 (br s, 1H), 3.52 (s, 2H), 3.48 (m, 3H), 3.02 (t, 2H), 2.05 (m, 4H), 1.79 (m, 4H).
IR (film) 3320, 2930, 1755, 1650, 1550 cm$^{-1}$.
Mass Spectrum (EI, m/z) 328 (M+), 237, 110, 91, 82.

C— Preparation of Dihydrothienopyridine 5

The amide (6, 1 equiv) and phosphorus oxychloride (2 equiv) were combined in benzene (25 mL/g POCl$_3$) and refluxed until TLC examination indicated the reaction was complete (typically 2-3 h). The reaction was allowed to cool and then cautiously poured into an equal volume of ice water. The resulting mixture was made strongly basic with 50% sodium hydroxide. The layers were separated and the aqueous layer was extracted with benzene (2×100 mL). The combined organic fractions were dried over sodium sulfate and concentrated in vacuo. The crude dihydrothieno-pyridine 5 was obtained as a dark oil (51%). This compound was used in the next step without further purification.

D—Preparation of Thienopyridine 4

The dihydrothienopyridine (5; 3.0 g) and a catalytic amount of palladium on carbon (5% by weight, 0.15 g) were combined neat in a flask with a magnetic stir bar. A sand bath was equilibrated to 220°-250° C. and the reaction, stirring under a nitrogen atmosphere, was set in the sand bath until TLC examination indicated consumption of starting material (typically 20-40 min). The crude reaction mixture was allowed to cool to room temperature and was purified by flash chromatography in 5% ethanol/chloroform yielding 1.34 g (45%) of compound 4.
$^1$H NMR (200 MHz, CDCl$_3$) δ 8.40 (d, 1H), 7.66 (d, 1H), 7.54 (d, 1H), 7.46 (d, 1H), 7.34 (m, 5H), 3.60 (s, 2H), 3.24 (m, 1H), 3.07 (d, 2H), 2.20 (t, 4H), 1.92 (m, 2H).
$^{13}$C NMR (50 MHz, CDCl$_3$) δ 160.6, 147.4, 142.1, 138.5, 133.6, 129.1, 128.1, 126.9, 126.3, 121.6, 115.3, 63.2, 58.2, 53.9, 42.4, 31.2, 18.4.
IR (film) 2960, 2800, 2760, 1575, 1545, 1500, 1430 cm$^{-1}$.
Mass spectrum (EI, m/z) 308 (M+), 217, 134, 91.

E—Preparation of Carbamate 3

Ethyl chloroformate (3 equiv) and potassium carbonate (2 equiv) were combined and stirred in dry benzene (5 mL/mL formate). The N-benzyl piperidine 4 (1 equiv) in benzene (same volume as above) was added dropwise through an addition funnel. TLC examination indicated the reaction was complete after 2-4 h. The reaction was concentrated in vacuo, taken up in methylene chloride, and extracted with water. The organic layer was dried over magnesium sulfate and concentrated in vacuo. The product carbamate 3 was purified by flash chromatography in 20% ethyl acetate in methylene chloride to yield 6.15 g (75%).
$^1$H NMR (200 MHz, CDCl$_3$) δ 8.40 (d, J=5.6 Hz, 1H), 7.68 (d, J=5.4 Hz, 1H), 7.51 (m, 2H), 4.36 (m, 2H), 4.16 (q, J=7.0 Hz, 2H), 3.42 (m, 1H), 2.98 (m, 2H), 2.00 (m, 4H), 1.28 (t, J=7.0 Hz, 3H).
$^{13}$C NMR (50 MHz, CDCl$_3$) δ 159.5, 155.5, 147.5, 142.0, 133.4, 126.8, 121.2, 115.5, 61.2, 44.2, 42.0, 30.9, 14.7.
IR (film) 3080, 2980, 1703, 1570, 1540, 1470, 1430, 1390 cm$^{-1}$.
Mass spectrum (DCI, m/z) 291 (M+H), 245, 163.

F—4-(4-Piperidinyl)thieno[3,2-c]pyridine III

Carbamate 3 (3.5 g, 1 equiv) was dissolved in a minimum of chloroform and warmed to 60° C. Iodotrimethylsilane (1.2 equiv) was added via syringe and the reaction was stirred until TLC examination indicated consumption of starting material (typically 3 h). While the reaction was maintained at 60° C., excess methanolic HCl was added resulting in $CO_2$ evolution. After 30 min, the reaction was concentrated to dryness in vacuo. The resultant solid was dissolved in sodium methoxide/methanol (1 equiv) and stirred briefly. The reaction was again concentrated to dryness in vacuo and the residue was partitioned between 10% aqueous $Na_2CO_3$ and chloroform. The layers were separated, the organic fraction was concentrated to dryness in vacuo and purified by flash chromatography in 5% ethanol/chloroform to yield the desired product (0.5 g, 11%) and recovered starting material (3.0 g, 85%). The product was converted to the hydrochloride salt and recrystallized from ethanol.

¹H NMR (300 MHz, DMSO-d₆) δ 9.60 (br s, 1H), 9.35 (br s, 1H), 8.38 (d, J=5.3 Hz, 1H), 7.93 (m, 3H), 3.75 (m, 1H), 3.42 (m, 2H), 3.16 (t, J=11.5 Hz, 2H), 2.23 (m, 2H), 2.00 (m, 2H).

¹³C NMR (75 MHz, DMSO-d₆) δ 158.4, 146.9, 141.6, 133.2, 128.1, 121.7, 115.9, 42.9, 38.3, 27.5.

IR (KBr) 3450, 2950, 2750, 2500, 1450, 730 cm⁻¹.

Mass spectrum (EI, m/z) 218 (M+), 190, 176, 162, 149, 134.

EXAMPLE 2

1,2,5,6-Dihydropyridine Intermediates

Preparation of 4-[4-(1,2,5,6-Tetrahydropyridinyl)-thieno[3,2-c]pyridine (III)

A—Preparation of Benzoate 14

To a −35° C. stirring slurry of sodium hydride (1.11 g, 1.2 equiv) in 50 mL anhydrous DMF was added Reissert compound 16 (New, et al., *J. Heterocyclic Chem* (1986) 23:545; 10.0 g, 1.0 equiv) in 100 mL anhydrous DMF. The addition was such that the internally monitored reaction temperature did not exceed −30° C. After stirring for 5-10 min, commercially available 1-benzyl-4-piperidone (7.5 g, 1.05 equiv) in 50 mL anhydrous DMF was added; the temperature again being kept below −30° C. The solution was allowed to slowly warm to room temperature overnight. The reaction was poured onto 1 L ice water. The precipitate was collected by filtration, dissolved in methylene chloride and washed with water (1×). The organic fraction was dried over sodium sulfate and the solvent was removed in vacuo. The resulting solid was recrystallized from ethyl acetate to afford 12.0 g (2 crops, 75%) of a white solid.

¹H NMR (CDCl₃) δ 8.4 (d, 1H), 3.05 (d, 1H), 7.8-7.1 (m, 12H), 3.6 (s, 2H), 3.0-2.4 (m, 8H).

¹³C NMR (CDCl₃) δ 179.0, 164.1, 158.0, 148.4, 141.0, 138.4, 132.9, 131.2, 130.5, 129.5, 128.9, 128.7, 128.4, 126.7, 122.0, 116.4, 83.6, 63.0, 49.4, 34.2.

IR (KBr) 3400, 2910, 1714, 1287, 1259, 719 cm⁻¹.

B—Preparation of Alcohol 13

Benzoate 14 (12.0 g) was refluxed for 24 h in 150 mL 6N HCl. The room temperature solution was slowly basified with 25% NaOH. The basic aqueous solution was extracted with chloroform (3×). The combined organic fractions were dried over sodium sulfate, filtered, and the solvent was removed in vacuo affording essentially pure 13 in quantitative yield as a golden oil.

¹H NMR (DMSO-d₆) δ 8.3 (d, J=3.5 Hz, 1H), 8.13 (d, J=3.5 Hz, 1H), 8.00 (d, J=3.5 Hz, 1H), 7.86 (d, J=3.5 Hz, 1H), 7.59-7.41 (m, 5H), 4.35 (s, 2H), 3.33 (m, 2H), 2.58 (m, 2H), 2.05 (m, 2H).

IR (KBr) 3450, 2750, 2550, 1610, 1380, 1240, 700 cm⁻¹.

C—preparation of Chloride 12

Alcohol 13 (500 mg, 1 equiv) was dissolved in 50 mL chloroform. The solution was stirred and thionyl chloride (180 mg, 1 equiv) was added dropwise. The solution was warmed to 50° C. and stirred overnight. The reaction was concentrated to dryness in vacuo and partitioned between methylene chloride and saturated aqueous sodium carbonate. The layers were separated and the organic fraction was dried over sodium sulfate, filtered, and the solvent was removed in vacuo. Flash chromatography in 50% ethyl acetate/hexane afforded 396 mg (75%) of the desired product.

D—Preparation of N-Benzyl Tetrahydropyridine 11

Chloride 12 (23.0 g, 1.0 equiv) was combined with DBU (20.4 g, 2 equiv) in 400 mL xylene and stirred at 100° C. until TLC examination indicated complete reaction (ca. 5 h). The reaction was concentrated to dryness in vacuo. The residue was dissolved in methylene chloride and extracted with water (1×). The organic solvent was removed in vacuo and the residue was flash chromatographed in 10% ethyl acetate/methylene chloride to afford 11.8 g (60%) of 11 as an oil.

¹H NMR (60 MHz, CDCl₃) δ 8.36 (d, 1H), 7.58 (d, 1H), 7.30 (m, 7H), 6.18 (m, 1H), 3.64 (s, 2H), 3.21 (m, 2H), 2.78 (br s, 4H).

E—Preparation of Carbamate 10

The procedure was identical to that used in the preparation of carbamate in Example 1, step E (vide supra). The product (10) was obtained in 33% yield from 11 following purification by flash chromatography in 50% ethyl acetate/methylene chloride.

¹H NMR (60 MHz, CDCl₃) δ 8.38 (d, 1H), 7.66 (d, 1H), 7.46 (m, 2H), 6.21 (m, 1H), 4.22 (m, 2H), 3.78 (t, 2H), 2.83 (m, 4H), 1.32 (t, 3H).

F—Preparation of 4-[4-(1,2,5,6-Tetrahydropyridinyl)]thieno[3,2-c]pyridine III The procedure was identical to that used in the Example 1, step F preparation of piperidine III (vide supra). The product (III) was obtained in 93% yield from 10 following purification by flash chromatography in 10% methanol/chloroform.

¹H NMR (DMSO-d₆) δ 9.8 (br s, 1H), 8.3 (d, 1H), 8.0 (d, 1H), 6.5 (m, 1H), 3.9 (m, 2H), 3.4 (m, 2H), 3.0 (m, 2H).

IR (KBr) 3400, 3055, 2750, 2454, 1733, 1600, 1380, 1240, 920 cm⁻¹.

Synthesis of Products of Formula I

EXAMPLE 3

4,4-Dimethyl-1-[4-[4-(thieno[3,2-c]pyridin-4-yl)-1-piperidinyl]butyl]-2,6-piperidinedione A mixture of 4-(4-piperidinyl)thieno[3,2-c]pyridine (III; 2.50 g, 1.00 equiv) and N-(4-bromobutyl)-3,3-dimethylglutarimide (New, et al. J. Med. Chem 1989, 32, 1147; 1.00 equiv) and potassium carbonate (3.00 equiv) was refluxed in acetonitrile (150 mL) for 24 h. The reaction was filtered hot and the solvent was removed in vacuo. The residue was flash chromatographed in a 1%-5% MeOH/CH₂CH₂ gradient. The chromatographed material was converted to the hydrochloride salt and recrystallized from acetonitrile/ethyl acetate as an off-white solid: mp 199°-202° C.

¹H NMR (DMSO-d₆) δ 8.38 (d, J=3.5 Hz, 1H), 7.95 (m, 3H), 3.71 (m, 3H), 3.61 (m 2H), 3.23 (m, 2H), 3.11 (m, 2H), 2.59 (s, 4H), 2.47 (m, 2H), 2.03 (m, 2H), 1,84 (m, 2H), 1.52 (m, 2H), 1.00 (S, 6H).

¹³C NMR (DMSO-d₆) δ 171.78, 158.03, 146.92, 141.56, 133.26, 128.08, 121.69, 115.92, 55.73, 51.46, 45.45, 38.88, 37.79, 28.63, 27.98, 27.02, 24.98, 20.55.

IR (KBr) 3450, 2980, 2500, 1730, 1690, 1450, 1390, 1150 cm⁻¹.

We claim:
1. A compound of Formula I

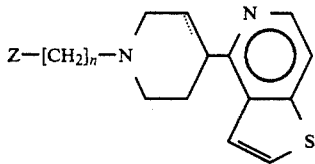

and the pharmaceutically acceptable acid addition salts and/or solvates thereof, wherein Z is

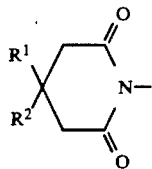

with $R^1$ and $R^2$ being independently selected from hydrogen and $C_{1-4}$ alkyl, or taken together as a $C_4$ or $C_5$ alkylene bridge; n is the integer 2, 3, or 4; and the dotted line accompanying a full line indicates a single or double bond.

2. The compound of claim 1 wherein $R^1$ and $R^2$ are independently selected from hydrogen and $C_{1-4}$ alkyl.

3. The compound of claim 1 wherein $R^1$ and $R^2$ are $C_{1-4}$ alkyl.

4. The compound of claim 1 wherein the dotted line accompanying a full line indicates a single bond.

5. The compound of claim 1, 4,4-Dimethyl-1-[4-[4-thieno[3,2-c]pyridin-4-yl)-1-piperidinyl]butyl]-2,6-piperidinedione.

6. The compound of claim 1, 4-Methyl-1-[4-[4-(thieno[3,2-c]pyridin-4-yl)-1-piperidinyl]butyl]-2,6-piperidinedione.

7. The compound of claim 1, 1-[4-[4-(Thieno[3,2-c]pyridin-4-yl]-1-piperidinyl]butyl]-2-piperidinedione.

8. The compound of claim 1, 4,4-Dimethyl-1-[4-[4-thieno[3,2-c]pyridin-4-yl)-1-(1,2,5,6-tetrahydropyridinyl)]butyl]-2,6-piperidinedione.

9. The method for ameliorating an undesirable psychotic state in a mammal comprising administration to the mammal in need of such treatment, an effective antipsychotic amount of a compound claimed in claim 1.

10. The method of claim 9 comprising the administration of 4,4-Dimethyl-1-[4-[4-(thieno[3,2-c]pyridin-4-yl)-1-piperidinyl]butyl]-2,6-piperidinedione.

11. A pharmaceutical composition in dosage unit form suitable for systemic administration to a mammalian host comprising a pharmaceutical carrier and an antipsychotic effective amount of a compound claimed in claim 1.

12. The pharmaceutical composition of claim 11 wherein the claim 1 compound is 4,4-Dimethyl-1-[4-[4-(thieno[3,2-c]pyridin-4-yl)-1-piperidinyl]butyl]-2,6-piperidinedione.

* * * * *